United States Patent [19]

Urdea

[11] Patent Number: 4,775,619

[45] Date of Patent: Oct. 4, 1988

[54] POLYNUCLEOTIDE DETERMINATION WITH SELECTABLE CLEAVAGE SITES

[75] Inventor: Mickey S. Urdea, San Francisco, Calif.

[73] Assignee: Chiron Corporation, Emeryville, Calif.

[21] Appl. No.: 661,508

[22] Filed: Oct. 16, 1984

[51] Int. Cl.[4] .................... G12Q 1/68; G01N 33/566; C12P 19/34

[52] U.S. Cl. ........................... 435/6; 435/803; 435/810; 435/91; 935/78; 436/501; 436/527; 536/27

[58] Field of Search ............ 435/6, 803, 91, 810; 935/78; 436/501, 518, 527, 532, 533, 824; 536/27

[56] References Cited

U.S. PATENT DOCUMENTS

| | | | |
|---|---|---|---|
| 4,032,659 | 6/1977 | Hegarty et al. | 514/582 |
| 4,146,454 | 3/1979 | Haber | 436/516 X |
| 4,230,797 | 10/1980 | Boguslaski et al. | 436/518 X |
| 4,358,535 | 11/1982 | Falkow et al. | 436/504 X |
| 4,395,486 | 7/1983 | Wilson et al. | 436/504 X |
| 4,419,444 | 12/1983 | Quash | 436/518 X |
| 4,430,432 | 2/1984 | Ando et al. | 435/199 |
| 4,469,796 | 9/1984 | Axén et al. | 436/518 |
| 4,486,539 | 12/1984 | Ranki et al. | 436/504 |
| 4,542,102 | 9/1985 | Dattagupta et al. | 935/78 X |
| 4,563,417 | 1/1986 | Albarella et al. | 935/77 X |
| 4,563,419 | 1/1986 | Ranki et al. | 436/504 X |
| 4,683,194 | 7/1987 | Saiki et al. | 436/808 X |

FOREIGN PATENT DOCUMENTS 0070687 1/1983 European Pat. Off. .

OTHER PUBLICATIONS

Dunn, A. R. et al., In *Methods in Enzymology*, vol. 65, Nucleic Acids, Part I, (L. Grossman et al., editor), Academic Press, N.Y., 1980, pp. 468-478.

Bauman, J. G. J. et al., J. Hist. Cytochem., vol. 29, No. 2, 1981, pp. 227-237.

Kennell, D. E., In: Progress in Nucleic Acid Research and Molecular Biology, (Davidson, J. E. et al., ed.), Academic Press, N.Y., 1971, pp. 259-263.

Primary Examiner—Charles F. Warren
Assistant Examiner—Jeremy M. Jay
Attorney, Agent, or Firm—Ciotti & Murashige, Irell & Manella

[57] ABSTRACT

Methods for diagnosis employing polynucleotides having oligonucleotide sequences substantially homologous to a sequence of interest, where the presence or absence of hybridization at a predetermined stringency provides for the release of a label from a support. Particularly, various techniques are employed for binding a label to a support, whereupon cleavage of either a single or double strand, a label may be released from a support, where the release of the label can be detected as indicative of the presence of a particular oligonucleotide sequence in a sample. The method finds use in diagnosis of disease, genetic monitoring, and analyzing nucleic acid mixtures.

25 Claims, 1 Drawing Sheet

"CARTOONS" OF POSSIBLE EMBODIMENTS

EMBODIMENT 1:

EMBODIMENT 3:

"CARTOONS" OF POSSIBLE EMBODIMENTS

EMBODIMENT 1:

EMBODIMENT 2:

Ⓐ
a)

b)

Ⓑ
a)

b)

EMBODIMENT 3:

FIG._I.

POLYNUCLEOTIDE DETERMINATION WITH SELECTABLE CLEAVAGE SITES

BACKGROUND OF THE INVENTION

1. Field of the Invention

The ability to synthesize oligonucleotide sequences at will and to clone polynucleotide sequences prepared by synthetic procedures or obtained from naturally occurring sources has greatly expanded the opportunities for detecting the presence of specific sequences in an extended oligonucleotide sequence, e.g., chromosome(s), mixture of sequences, mRNAs, or the like. Interest in specific sequences may involve the diagnosis of the presence of pathogens, the determination of the presence of alleles, the presence of lesions in a host genome, the detection of a particular mRNA or the monitoring of a modification of a cellular host, to mention only a few illustrative opportunities. While the use of antibodies to perform assays diagnostic of the presence of various antigens in samples has seen an explosive expansion in techniques and protocols since the advent of radioimmunoassay, there has been until recently no parallel activity in the area of DNA probes. Therefore, for the most part, detection of sequences has involved various hybridization techniques requiring the binding of a polynucleotide sequence to a support and employing a radiolabeled probe.

In view of the increasing capability to produce oligonucleotide sequences in large amounts in an economical way, the attention of investigators will be directed to providing for simple, accurate and efficient techniques for detecting specific oligonucleotide sequences. Desirably, these techniques will be rapid, minimize the opportunity for technician error, be capable of automation, and allow for simple and accurate methods of detection. Toward this end, there have already been efforts to provide for means to label oligonucleotide probes with labels other than radioisotopes and for improving the accuracy of transfer of DNA sequences to a support from a gel, as well as improved methods for derivatizing oligonucleotides to allow for binding to a label. There continues to be a need for providing new protocols which allow for flexibility in detecting DNA sequences of interest in a variety of situations where the DNA may come from diverse sources.

2. Description of the Prior Art

Meinkoth and Wahl, Anal. Biochemistry (1984) 138:267-284, provide an excellent review of hybridization techniques. Leary et al., Proc. Natl. Acad. Sci. USA (1983) 80:4045-4049, describe the use of biotinylated DNA in conjunction with an avidin-enzyme conjugate for detection of specific oligonucleotide sequences. Ranki et al., Gene (1983) 21:77-85 describe what they refer to as a "sandwich" hybridization for detection of oligonucleotide sequences. Pfeuffer and Helmrich, J. of Biol. Chem. (1975) 250:867-876 describe the coupling of guanosine-5'-0-(3-thiotriphosphate) to Sepharose 4B. Bauman et al., J. of Histochem. and Cytochem. (1981) 29:227-237, describe the 3'-labeling of RNA with fluorescers. PCT Application WO 83 02277 describes the addition to DNA fragments of modified ribonucleotides for labeling and methods for analyzing such DNA fragments. Renz and Kurz, Nucl. Acids Res. (1984) 12:3435-3444, describe the covalent linking of enzymes to oligonucleotides. Wallace, DNA Recombinant Technology (Woo, S., Ed.) CRC Press, Boca Raton, Florida, provides a general background of the use of probes in diagnosis. Chou and Merigan, N. Eng. J. of Med. (1983) 308:921-925, describe the use of a radioisotope labeled probe for the detection of CMV. Inman, Methods in Enzymol. 34B, 24 (1974) 30-59, describes procedures for linking to polyacrylamides, while Parikh et al., Methods in Enzymol. 34B, 24 (1974) 77-102, describe coupling reactions with agarose. Alwine et al., Proc. Natl. Acad. Sci. USA (1977) 74:5350-5354, describe a method of transferring oligonucleotides from gels to a solid support for hybridization. Chu et al., Nucl. Acids Res. (1983) 11:6513-6529, describe a technique for derivatizing terminal nucleotides. Ho et al., Biochemistry (1981) 20:64-67, describe derivatizing terminal nucleotides through phosphate to form esters. Ashley and MacDonald, Anal. Biochem. (1984) 140:95-103, report a method for preparing probes from a surface bound template. These references which describe techniques are incorporated herein by reference in support of the preparation of labeled oligonucleotides.

SUMMARY OF THE INVENTION

Methods are provided for the detection of specific nucleotide sequences employing a solid support, at least one label, and hybridization involving a sample and a labeled probe, where the presence or absence of duplex formation results in the ability to modify the spatial relationship between the support and label(s). Exemplary of the technique is to provide a cleavage site between the label and support through duplexing of a labeled probe and sample DNA, where the duplex is bound to a support. The cleavage site may then be cleaved resulting in separation of the support and the label(s). Detection of the presence or absence of the label may then proceed in accordance with conventional techniques.

DESCRIPTION OF THE SPECIFIC EMBODIMENTS

Detection of specific sequences is achieved using hybridization, whereby duplexing of the sample DNA and a probe affects the ability to modify the spatial relationship between a label and a support. In this manner, the presence or absence of a particular sequence in a sample can be readily determined by the amount of label which is freed into the medium.

The subject method allows for varying protocols and reagents where the sample nucleic acid may be bound to a support or free in solution. The method involves forming a nucleic acid duplex where a label is separated from a support by a selectively cleavable bond, so that the amount of label released under conditions providing selective cleavage is a measure of the presence and amount of a sequence of interest in a nucleic acid sample. The selectable cleavage site may be as a result of formation of a restriction enzyme recognition site through homoduplexing or the presence of such selectable cleavage site in the single-stranded polynucleotide chain bound to the support or bound to the label, as a result of the prior introduction of such site in the single-stranded chain.

A reagent will be employed which will include a polynucleotide sequence which has an oligonucleotide sequence of interest which hybridizes with the nucleic acid analyte. A labeled probe will be employed, which may or may not include the sequence of interest and may or may not be bound to the support. The reagent may have one or two polynucleotide components.

The subject method involves the forming of a polynucleotide duplex in a hybridization medium resulting in a label bound to a support through a selectable cleavage site. Various protocols may be employed where the sample DNA is bound to a support or a dispersed in solution.

In order to distinguish the various nucleotide sequences involved, the following terms will be used:

nucleic acid sample—sample suspected of containing a nucleic acid sequence having an oligonucleotide sequence of interest;

nucleic acid analyte—DNA or RNA in said nucleic acid sample having an oligonucleotide sequence of interest;

oligonucleotide sequence of interest—a DNA or RNA sequence which may be all or part of a nucleotide chain, usually at least six bases, more usually at least about 10 bases, preferably at least about 16 bases, which may be 5 kb or more, usually not more than about 0.2 kb, which is diagnostic of a property to be detected, where the property may be a gene or sequence diagnostic of a hereditary trait, pathogen, etc.;

polynucleotide sequence—DNA or RNA sequences employed as reagents for detection of the oligonucleotide sequence of interest, which polynucleotide sequence may be labeled or unlabeled, bound or unbound to a support, and may or may not include a sequence complementary to the oligonucleotide sequence of interest. There will be one to two polynucleotide sequences, which individually or in conjunction with the nucleic acid analyte will act as a bridge between a label and a support, with a selectably cleavable site intermediate the label and support; and selectably cleavable site—a functionality or plurality of functionalities which can be selectively cleaved and may include restriction sites, phosphate esters, purines, peptide bonds, etc.

For convenience of description, the subject invention will be divided into three embodiments. In the first embodiment (see FIG. 1) the reagent employed is a single component, which is a polynucleotide joined proximal to one end to a support and joined proximal to the opposite end to one or more detectable labels. The polynucleotide will include a region of at least four successive nucleotides homoduplexing with a sequence of interest, where such sequence includes a restriction site, which is intermediate the support and label.

Figure 1:
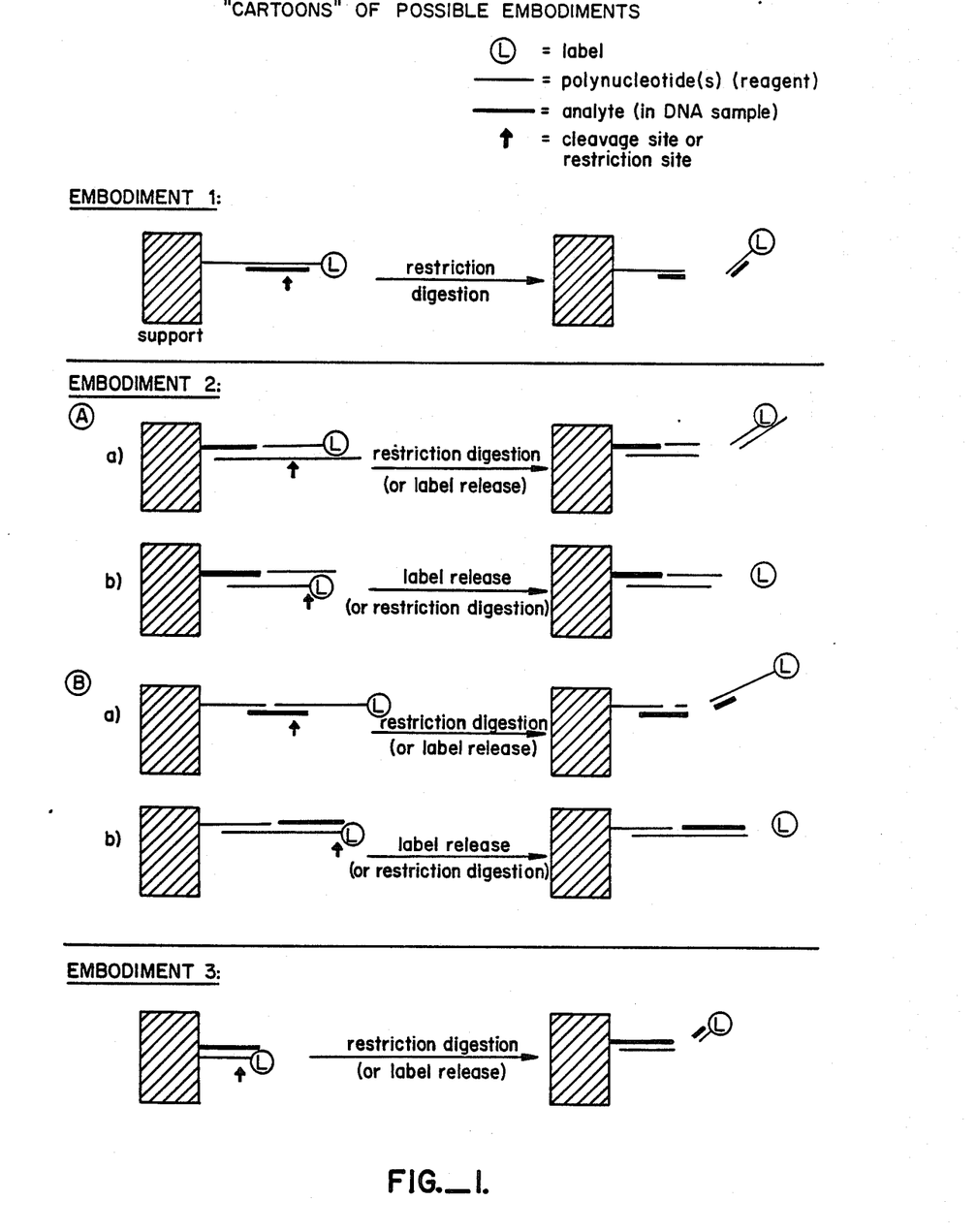
FIG. 1 is a cartoon of different embodiments of the subject methods.

In the second embodiment (see FIG. 1) the reagent employed will have two components which will vary with whether the nucleic acid sample is bound or unbound to a support and the nature of the selectable cleavage site. Where the nucleic acid sample is bound to the support, the two components will be (1) a bridging polynucleotide sequence and (2) a polynucleotide sequence complementary and hybridizing to a portion of the bridging polynucleotide sequence. Either the bridging or complementary polynucleotide sequence may be labeled. The presence of the label bound to the bridging sequence will be limited to when the duplex of the bridging and analyte polynucleotide sequences define a restriction site as the selectable cleavage site. Otherwise, only the complementary sequence will be labeled. Besides having a sequence duplexing with the complementary sequence, the bridging polynucleotide sequence will have a region duplexing with the oligonucleotide sequence of interest.

Where the sample nucleic acid is in solution, the two components will be (1) a first polynucleotide sequence bound to a support, which has a region complementary to a sequence present in the nucleic acid analyte, which sequence may or may not define a restriction site and may or may not define the oligonucleotide sequence of interest; and (2) a labeled second polynucleotide sequence which has a region complementary to a sequence present in the nucleic acid analyte, which region is subject to the same limitations as the region of the first polynucleotide sequence. At least one of the duplexed regions will define a sequence of interest. In the absence of one of the regions defining a restriction site or in addition to the presence of a restriction site, there will be a selectable cleavage site present with the first or second polynucleotide sequence.

In the third embodiment (see FIG. 1) the analyte is bound to a support and the reagent employed is a single component which is a labeled polynucleotide sequence having a region complementary to the oligonucleotide sequence of interest which may define a restriction site. The restriction site and/or a functionality present on the labeled polynucleotide sequence may serve as a selectable cleavage site.

The nucleic acid containing sample will be combined with the appropriate reagent under conditions where duplex formation occurs between complementary sequences. The mixture is allowed to hybridize under conditions of predetermined stringency to allow for at least heteroduplex formation or homoduplex formation over an oligonucleotide sequence of interest. After a sufficient time for hybridization to occur, the support may be separated from the supernatant and washed free of at least substantially all of the non-specifically bound label. The oligonucleotides bound to the support are then treated with one or more reagents, which results in cleavage of at least one strand and release of label bound to support.

Depending upon the presence of a particular sequence in the sample resulting in duplex formation, release of the label(s) bound to the support will be observed. Various protocols may be employed, where normally the supernatant medium may be assayed for the presence of the label, although in some instances the support may be measured. Protocols and reagents may be employed, where a physical separation of the support from the supernatant may or may not be required.

The subject method can be used for the detection of oligonucleotide sequences, either DNA or RNA, in a wide variety of situations. One important area of interest is the detection of pathogens, viruses, bacteria, fungi, protozoa, or the like, which can infect a particular host. See for example, U.S. Pat. No. 4,358,535. Another area of interest is the detection of alleles, mutations or lesions present in the genome of a host, such as involved in amniocentesis, genetic counseling, host sensitivity or susceptibility determinations, and monitoring of cell populations. A third area of interest is the determination of the presence of RNA for such diverse reasons as monitoring transcription, detecting RNA viruses, differentiating organisms through unexpressed RNA, and the like. Other areas of interest, which are intended to be illustrative, but not totally inclusive, include monitoring modified organisms for the presence of extrachromosomal DNA or integrated DNA, amplifications of DNA sequences, and maintenance of such sequences.

The physiological samples may be obtained from a wide variety of sources as is evident from the varied purposes for which the subject method may be used. Sources may include various physiological fluids, such as excreta, e.g., stool, sputum, urine, saliva, etc.; plasma, blood, serum, ocular lens fluid, spinal fluid, lymph, and the like. The sample may be used without modification or may be modified by expanding the sample, cloning, or the like, to provide an isolate, so that there is an overall enhancement of the DNA or RNA and reduction of extraneous RNA or DNA. Viruses may be plated on a lawn of compatible cells, so as to enhance the amount of viral DNA; clinical isolates may be obtained by the sample being streaked or spotted on a nutrient agar medium and individual colonies assayed; or the entire sample introduced into a liquid broth and the cells selectively or non-selectively expanded. The particular manner in which the sample is treated will be dependent upon the nature of the sample, the nature of the DNA or RNA source, the amount of oligonucleotide sequence of interest which is anticipated as being present as compared to the total amount of nucleic acid present, as well as the sensitivity of the protocol and label being employed.

Either the sample nucleic acid or the reagent polynucleotide may be bound, either covalently or non-covalently, but in any event non-diffusively, to the support. Where a sample nucleic acid is bound to the support, various supports have found particular use and to that extent, those supports will be preferred. These supports include nitrocellulose filters, diazotized paper, ecteola paper, or other support which provides such desired properties as low or no non-specific binding, retention of the nucleic acid sample, ease of manipulation, and allowing for various treatments, such as growth of organisms, washing, heating, transfer, and label detection, as appropriate.

To the extent that a component of the polynucleotide reagent is bound to the support, the type of support may be greatly varied over the type of support involved with the sample oligonucleotide. The support may include particles, paper, plastic sheets, container holder walls, dividers, millipore filters, etc., where the materials may include organic polymers, both naturally occurring and synthetic, such as polysaccharides, polystyrene, polyacrylic acid and derivatives thereof, e.g., polyacrylamide, glass, ceramic, metal, carbon, polyvinyl chloride, protein, and the like. The various materials may be functionalized or non-functionalized, depending upon whether covalent or non-covalent bonding is desired.

Where the sample nucleic acid is bound to the support, depending upon the particular support, heating may be sufficient for satisfactory binding of the nucleic acid. In other situations, diazo groups may be employed for linking to the nucleic acid. Where, however, the polynucleotide reagent component is bound to the support, a wide variety of different techniques may be employed for ensuring the maintenance of the polynucleotide reagent bound to the support. For example, supports can be functionalized, to have active amino groups for binding, resulting from the binding of alkylamines, hydrazides, or thiosemicarbazides to the support. One can then add, by means of a terminal transferase, a ribonucleotide to a DNA polynucleotide reagent. Upon glycol cleavage with an appropriate oxidant, e.g., periodate, osmium tetroxide plus hydrogen peroxide, lead tetraacetate, or the like, a dialdehyde is formed, which will then bind to the amino group on the surface to provide a monosubstituted amino or disubstituted amino group. Alternatively, one can provide for a maleimide group which with thiophosphate will form the alkylthioester. Various techniques described by Parikh et al., supra and by Inman, supra for agarose and polyacrylamide may be employed, which techniques may have application with other materials.

The total number of polynucleotide reagent components of the support available in the assay medium will vary, for the most part being determined empirically. Desirably, a relatively high concentration per unit surface area of polynucleotide to available functional groups on the support should be employed, so long as the polynucleotide density does not interfere with hybridization.

The size of the polynucleotide will vary widely, usually being not less than about 15 bases and may be 50 bases or more, usually not exceeding about 500 bases, more usually not exceeding 250 bases. There will usually be a region in the polynucleotide reagent component homologous with a sequence in the nucleic acid sample, usually the sequence of interest, of at least six bases, usually at least 12 bases. The region for hybridization may be 16 bases or more, usually not exceeding about 1 kbp, where perfect homology is not required, it being sufficient that there be homology to at least about 50%, more preferably homology to at least 80%. By percent homology is intended complementarity, ignoring non-complementary insertions which may loop out, insertions being greater than five bases.)

Particularly, where one is interested in a group of allelic genes, a number of different strains, or related species, where the messenger RNA or genomic portion is highly conserved but nevertheless is subject to polymorphisms, it will frequently be desirable to prepare a probe which reflects the differences and optimizes the homology for all the sequences of interest, as against any particular sequence.

The label of the labeled polynucleotide reagent component may be joined to the polynucleotide sequence through the selectively cleavable site or through a link which is retained during the assay. A wide variety of labels may be employed, where the label may provide for a detectable signal or means for obtaining a detectable signal.

Labels therefore include such diverse substituents as ligands, radioisotopes, enzymes, fluorescers, chemiluminescers, enzyme suicide inhibitors, enzyme cofactors, enzyme substrates, or other substituent which can provide, either directly or indirectly, a detectable signal.

Where ligands are involved, there will normally be employed a receptor which specifically binds to the ligand, e.g., biotin and avidin, 2,4-dinitrobenzene and anti(2,4-dinitrobenzene)IgG, etc., where the receptor will be substituted with appropriate labels, as described above. In this manner, one can augment the number of labels providing for a detectable signal per polynucleotide sequence.

For the most part, the labels employed for use in immunoassays can be employed in the subject assays. These labels are illustrated in U.S. Pat. Nos. 3,850,752 (enzyme); 3,853,914 (spin label); 4,160,016 (fluorescer); 4,174,384 (fluorescer and quencher); 4,160,645 (catalyst); 4,277,437 (chemiluminescer); 4,318,707 (quenching particle); and 4,318,890 (enzyme substrate).

Illustrative fluorescent and chemiluminescent labels include fluorescein, rhodamine, dansyl, umbelliferone, biliproteins, luminol, etc.

Illustrative enzymes of interest include horse radish peroxidase, glucose-6-phosphate dehydrogenase, acetylcholinesterase, β-galactosidase, α-amylase, uricase, malate dehydrogenase, etc. That is, the enzymes of interest will primarily be hydrolases and oxidoreductases.

The manner in which the label becomes bound to the polynucleotide sequence will vary widely, depending upon the nature of the label. As already indicated, a ribonucleotide may be added to the oligonucleotide sequence, cleaved, and the resulting dialdehyde conjugated to an amino or hydrazine group. The permanence of the binding may be further enhanced by employing reducing conditions, which results in the formation of an alkyl amine. Alternatively, the label may be substituted with an active halogen, such as alpha-bromo or -chloroacetyl. This may be linked to a thiophosphate group or thiopurine to form a thioether. Alternatively, the label may have a maleimide functionality, where a mercapto group present on the polynucleotide will form a thioether. The terminal phosphate of the polynucleotide may be activated with carbodiimide, where the resulting phosphorimidazolide will react with amino groups or alcohols to result in phosphoramidates or phosphate esters. Polypeptide bonds may be formed to amino modified purines. Thus, one has a wide latitude in the choice of label, the manner of linking, and the choice of linking group.

By combining the polynucleotide reagent with the sample, andy nucleic acid analyte present will become bound to the support. The amount of label released from the support upon cleavage of the selectable cleavage site will be related to the presence of analyte, where the amount of analyte may also be determined quantitatively.

The modification of the spatial relationship between the label and the support can be achieved in a number of ways. As indicated, there can be at least one recognition site common to the probe and the sample polynucleotide, which can be digested with a restriction enzyme, thus releasing the probe from the support. A wide variety of restriction enzymes are available which can detect four base, six base, or eight base recognition sites, where cleavage can be blunt-ended or staggered, may occur at the recognition site or distant from the recognition site. In this manner, the duplex formation of the recognition site(s) provides for the opportunity to cleave the double strand with release of the label.

The nature of the selective cleavage site may or may not depend upon the linking group. Where a restriction site is involved, the bonds involved with the reagent components need only be stable under the assay conditions. Where a restriction site is not involved, then the site will involve a bond(s) which allows for separation of the label from the support.

A phosphodiesterase may be employed where random hydrolysis will separate the label from the support. The polynucleotide may be tailed with modified nucleotides which are or may be subsequently labeled.

A wide variety of linking groups can be employed, where the nucleotides may be modified or unmodified for linkage of the label. WO 83/02277 reports the use of 8-aminoalkyladenosine, where a label can be bound to the amino group. The DNA polynucleotide reagent may then be tailed with the ribonucleotides so that a plurality of labels will be present at the terminus of each labeled polynucleotide. The tailed ribonucleotides may be selectively cleaved employing an RNase. This will be particularly advantageous when employing labels which interact to modify the signal. For example, fluorescers in close proximity tend to self-quench. The observed fluorescent signal can be greatly enhanced by hydrolysing the phosphate bonds, so that the individual fluorescer molecules are randomly present in solution. Of course, fluorescers need not be the only labels demonstrating this phenomenon, but other of the labels may also display similar effects. Where enzyme substrates or cofactors are employed, their presence on a polymer bound to a support will result in substantial steric interference with enzyme approach. Thus the depolymerization of the label and release from the support will substantially enhance the enzyme rate.

Another technique is to add a ribonucleotide to a DNA polynucleotide reagent and then cleave the ribosyl moiety to produce a dialdehyde. (See, for example, Lee et al, *Biochemistry* (1970) 9:113-118.) The dialdehyde may be linked to an amino group joined to a label through a selectively cleavable site. For example, a disulfide link may be present between the Schiff's base and the label which can be cleaved by reduction, with Ellman's reagent, or the like, to release the label. Where a restriction endonuclease will be used for release of the label, then the dialdehyde can be combined with the amino functionality under reductive amination conditions. Various amino sources, such as proteins, e.g., enzymes, phycobiliprotein fluorescers, receptors, such as immunoglobulins or avidin, or non-proteinaceous labels may be employed.

Another linking method involves activating a terminal phosphate with carbodiimide to form a phosphorimidazolide. (Chu et al., *Nucleic Acids Res.* (1983) 11:6513-6628.) The phosphorimidazolide may be reacted with amines to form phosphoramidates. As before, the amino linking group will include the selectable cleavage site, as appropriate, which could be a pyrophosphate diester, cleavable by a pyrophosphatase, a short polypeptide which could be cleaved by a peptidase, a light-sensitive functionality such as azo, peroxy, or the like.

Another method for attaching a label involves chemical synthesis of polynucleotides with a modifyable nucleoside derivative such as a cytosine or uracil containing a 12-atom amine linker arm, followed by incorporation of a reporter group such as fluorescein or dinitrobenzene (Ruth, *DNA* (1984) 3:123).

Ligand substituted nucleotides can be employed where the ligand does not give a detectable signal directly, but bonds to a receptor to which is conjugated to one or more labels. Illustrative examples include biotinylated nucleotides which will bind to avidins, haptens which will bind to immunoglobulins, and various naturally occurring compounds which bind to proteinaceous receptors, such as sugars with lectins, hormones and growth factors with cell surface membrane proteins, and the like.

A wide variety of supports and techniques for non-diffusive binding of oligonucleotide chains have been reported in the literature. For a review, see Meinkoth and Wahl, *Anal. Biochem.* (1984) 138:267-284. Supports include nitrocellulose filters, where temperatures of 80° C. for 2 hr suffices, diazotized papers, where bonding occurs without further activation, ecteola paper, etc. Agarose beads can be activated with cyanogen bromide for direct reaction with DNA. (Bauman et al., *J. Histochem. Cytochem.* (1981) 29:227–237); or reacted with cyanogen bromide and a diamine followed by reaction with an α-haloacetyl, e.g., bromoacetyl or with an active carboxylic substituted olefin, e.g., maleic anhydride, to provide beads capable of reacting with a thiol functionality present on a polynucleotide chain. For example, DNA can be modified to form a α-thiophosphate for coupling. (Pfeuffer and Hilmreich, *J. Biol. Chem.* (1975) 250:867–876.) It is also possible to synthesize by chemical means an oligonucleotide bound to a Teflon support and then fully deblock the material without removing it (Lohrmann et al., *DNA* (1984) 3:122).

In view of the wide diversity of labels and reagents, the common aspects of the method will be described, followed by a few exemplary protocols. Common to the procedures will be hybridization. The hybridization can be performed at varying degrees of stringency, so that greater or lesser homology is required for duplexing. For the most part, aqueous media will be employed, which may have a mixture of various other components. Particularly, organic polar solvents may be employed to enhance stringency. Illustrative solvents include dimethylformamide, dimethylacetamide, dimethylsulfoxide, that is, organic solvents which at the amounts employed, are miscible with water. Stringency can also be enhanced by increasing salt concentration, so that one obtains an enhanced ionic strength. Also, increasing temperature can be used to enhance stringency. In each case, the reverse direction results in reduced stringency. Other additives may also be used to modify the stringency, such as detergents.

The period of time for the hybridization will vary with the concentration of the sequence of interest, the stringency, the length of the complementary sequences, and the like. Usually, the hybridization requires at least about 15 min, and generally not more than about 72 hr, more usually not more than about 24 hr. Furthermore, one can provide for hybridization at one stringency and then wash at a higher stringency, so that heteroduplexes lacking sufficient homology are removed.

The nucleic acid sample will be treated in a variety of ways, where one may employ the intact genome, mechanically sheared or restriction enzyme digested fragments of the genome, varying from about 0.5 kb to 30 kb, or fragments which have been segregated according to size, for example, by electrophoresis. In some instances, the sequences of interest will be cloned sequences, which have been cloned in an appropriate vector, for example, a single-stranded DNA or RNA virus, e.g., M13.

Included in the assay medium may be other additives including buffers, detergents, e.g., SDS, Ficoll, polyvinyl pyrrolidone and foreign DNA, to minimize non-specific binding. All of these additives find illustration in the literature, and do not need to be described in detail here.

In accordance with a particular protocol, the sample nucleic acid and polynucleotide reagent(s) are brought together in the hybridization medium at the predetermined stringency. After a sufficient time for hybridization, the support will be washed at least once with a medium of greater or lesser stringency than the hybridization medium. The support with the bound polynucleotide and analyte will then be contacted with the necessary reactants (includes physical treatment, e.g., light) for cleaving the selectable cleavage site, providing for single- or double-stranded cleavage. For the most part hydrolase enzymes will be used, such as restriction endonucleases, phosphodiesterases, pyrophosphatase, peptidases, esterases, etc., although other reagents, such as reductants, Ellman's reagent, or light may find use. After cleavage, the support and upon the supernatant may or may not be separated, depending upon the label and the manner of measurement, and the amount of label released from the support determined.

To further illustrate the subject invention, a few exemplary protocols will be described. In the first exemplary protocol, a microtiter plate is employed, where fluorescent labeled polynucleotides are bound to the bottom of each well. DNA from a pathogen which has been cloned, is restricted with one or more restriction enzymes to provide fragments of from about 0.5 to 2 kb. The fragments are isolated under mild basic conditions for denaturing and dispersed in the hybridization medium, which is then added sequentially to the various wells, each of the wells having different sequences which are specifically homologous with sequences of different strains of a particular pathogen species.

The wells are maintained at an elevated temperature, e.g., 60° C., for sufficient time for hybridization to occur, whereupon the supernatant is removed and the wells are thoroughly washed repeatedly with a buffered medium of lower stringency than the hybridization medium. Duplex formation results in a recognition site for a restriction enzyme common to all of the strains. To each well is then added a restriction enzyme medium for digestion of double-stranded DNA having the recognition site. Those double-stranded DNAs which are digested result in the release of the fluorescent label into the supernatant. The supernatant is aspirated from each of the wells and irradiated. The amount of fluorescence is then determined as indicative of the presence of the sequence of interest. In this manner, one can rapidly screen for which of the strains is present, by observing the presence of fluorescence in the liquid phase.

In the second exemplary protocol, one employs a column containing glass beads to which are bound unlabeled polynucleotide. To the column is then added the sample nucleic acid containing DNA fragments obtained from mammalian cells. The fragments range from about 0.5 to 10 kb. The sample DNA is dispersed in an appropriate hybridization medium and added to the column and retained in the column for sufficient time for hybridization to occur. After the hybridization of the sample, the hybridization medium is released from the column and polynucleotide reagent labeled with horse radish peroxidase (HRP) through a disulfide linkage is added in a second hybridization medium under more stringent conditions than the first medium and the second medium released in the column for sufficient time for hybridization to occur. The labeled polynucleotide has a sequence complementary to the sequence of interest. The hybridization medium is evacuated from the column.

The column may then be washed one or more times with a medium of higher stringency to remove any polynucleotide sequences which have insufficient homology with the labeled polynucleotide. Ellman's reagent is then added to the column resulting in cleavage of the disulfide linkage and release of the HRP. The HRP containing medium is evacuated from the column and collected, as well as a subsequent wash to ensure that freed enzyme is not held up in the column. The resulting medium which contains the HRP label may now be assayed for the HRP label. Instead of HRP a wide variety of other enzymes can be used which produce products which can be detected spectrophotometrically or fluorometrically.

In a third protocol, the nucleic acid sample is non-diffusively bound to one end of a nitrocellulose filter by absorbing the sample with the filter and heating at 80° C. for 2 hr. The filter is washed and then added under hybridization conditions to a hybridization solution of a polynucleotide labeled with umbelliferone through an ester linkage to an alkylcarboxy substituted adenine. The labeled polynucleotide has a sequence complementary to the sequence of interest. After sufficient time for hybridization the filter is removed from the hybridization medium, washed to remove non-specifically bound nucleotides, and then submerged in a measured solution of an esterase. The rate of increase of fluorescence is monitored as a measure of the amount of analyte in the nucleic acid sample.

In another protocol, a dipstick can be used of a plastic material where a holder is employed which holds a strip having a labeled polynucleotide sequence complementary to the analyte sequence with a polyfluoresceinylated terminus. The nucleic acid sample is prepared in the appropriate hybridization medium and the dipstick introduced and hybridization allowed to proceed. After sufficient time for the hybridization to have occurred, the dipstick is removed and washed to remove any non-specific binding polynucleotide. The presence of a polynucleotide sequence of interest results in the formation of a restriction enzyme recognition site and the dipstick is then introduced into the restriction enzyme reaction mixture and digestion allowed to proceed. After sufficient time for digestion to have proceeded, the dipstick is removed, thoroughly washed, and the fluorescence in the solution read, where fluorescence above a baseline value indicates the presence of the analyte.

In another protocol, the polynucleotide reagent components are a first polynucleotide which has a sequence complementary to one region of the nucleic acid analyte and is bound to the walls of wells of a microtiter plate and a labeled second polynucleotide which has a sequence complementary to another region of the nucleic acid analyte. The label is the result of tailing the polynucleotide with $N^8$-aminohexyl deoxyadenosine triphosphate umbelliferyl carboxamide. The nucleic acid sample is introduced into the wells with an excess of the labeled polynucleotide under hybridizing conditions. After sufficient time for hybridization, the hybridization solution is aspirated out of the wells, the wells washed and the residual DNA in the wells depurinated by adding a solution of 90% formic acid and heating at 60° C. for 1 hr or adding piperidine and heating at 90° C. for 30 min.

Alternatively, the label can be a result of ligating the polynucleotide to be labeled with an excess of an oligomer obtained by treating poly-dA with chloroacetaldehyde according to Silver and Feisht, Biochemistry (1982) 21:6066 to produce the fluorescent $N^6$-ethenoadenosine. Release of the label is achieved with micrococcal nuclease in a solution of 100 μM $CaCl_2$ for 1 hr at 37° C.

In both instances the fluorescence of the polymer is substantially diminished due to self-quenching. Upon dissolution, a substantial enhancement in fluorescence is observed. Thus, non-specifically bound labeled polynucleotide resistant to the depolymerization would not interfere with the observed signal. Furthermore, one could measure the rate of increase of fluorescence as a quantitative measure of nucleic acid analyte, since the background fluorescent level would be low. Instead of self quenching, systems can be employed where fluorescers and quenchers alternate or in two component reagent systems, non-quenching fluorescers are present on one component and quenchers are present on the other component.

The following examples are offered by way of illustration and not by way of limitation.

EXPERIMENTAL

I. Attachment of ribonucleotides to the 3'-end of DNA.

a. Tailing with terminal deoxynucleotide transferase (TdT).

The following is a modification of the method described by R. Roychoudry, Methods in Enzymology (1980) 65:43. A synthetic oligonucleotide of the composition (5' to 3') ATTCGACGCTTATGG (fragment 1) was tailed with rATP. To a solution of 4005 pmoles of fragment 1 (based on 20 $OD_{260}$ units per mg) in 15 μl of 0.83 mM ATP, 2.5 μl of 10× TdT buffer (1.4M potassium cacodylate, 0.6M Tris pH 7.6, 10 mM $CoCl_2$, 1 mM dithiothreitol (DTT)), 2 μl of TdT (calf thymus, P-L Biochemicals, Inc.; 13.5 units) is added. The 24.5 μl sample was left for 1 hr at 37° C., then evaporated to dryness The pellet was dissolved in 10 μl of 90% formamide, 0.05% bromophenol blue, 1% Ficoll, heated to 90° C. for 5 min and loaded on a 20% denaturing polyacrylamide gel run at 40 ma. A band corresponding to fragment 1 extended by one riboadenosine unit was visualized by U.V. shadowing, cut from the gel and eluted overnight in 0.1M Tris pH 8.0, 5 mM EDTA, 0.5 m NaCl (Maxam and Gilbert, Methods in Enzymology (1980). 65:499–560). Desalting was achieved with a C-18 SEP-PAK (Waters Associates) as follows: The cartridge was first washed with 5 ml of reagent grade methanol then 10 ml of distilled water. The filtered sample was then applied by syringe to the SEP-PAK. After washing with 20 ml of water, the DNA was eluted with 3 ml of 1:1 (V:V), triethylamine acetate, pH 7.3 : methanol. The solution was then evaporated to dryness (yield ≃80%).

b. Ligation with $T_4$ ligase.

The following process was used to produce a 137 base fragment that contained a 3'-terminal riboadenosine. Fragment 1 from above is used as a "universal" adaptor in order to produce by ligation a ribonucleotide tailed DNA sequence.

Fragment 2

AGTTGGCAGTACAGCCTAGCAGCCAJG-
GAAACGATGTATATTTCCGCGAGAG-
GACGACAG

Fragment 3

GGTCGTCCGCGGGATTCAGCGCCGACG-
GGACGTAAACAAAGGACGTCCCG-
CGAAGGATCC

Fragment 4

TTCCATGGCTGCTAGGCTGTACTG-
CCAACTGGATCCTTCGCG-
GGACGTCCTTTGTTTACG

Fragment 5

AATTCTGTCGTCCTCTCGCG

Fragment 6

CCATAAGCGTCG

All sequences unless otherwise indicated were 5', 3' hydroxyl. The sequences can be ligated as follows:

(1) ligation
(2) gel isolation

Fragment 2 was 5' phosphorylated with T4 polynucleotide kinase. To 900 pmoles of the fragment that had been evaporated to dryness were added 2 μl of 10× KB-TS (500 mM Tris, 100 mM MgCl2, 10 μg/ml spermidine), 2 μl 10 mM ATP, 2 μl 10 mM DTT, 1 μl (8 units) T4 kinase (New England Nuclear) and 13 μl of water. After 30 min at 37° C., another 8U of T4 kinase were added. After an additional 30 min at 37° C., 45 μl (990 pmoles) of fragment 1 that had previously been 5'-phosphorylated in a similar manner were added. After adding 22 μl of 2M sodium acetate and 8 μl of 250 mM EDTA, the solution was heated for 5 min at 65° C. to inactivate the T4 kinase. Fragments 3 through 6 were dthen added (2.6 μl, 902 pmoles; 8 μl, 1008 pmoles; 32 μl, 1003 pmoles; 45 μl, 936 pmoles, respectively). The solution was vortexed, 680 μl of cold ethanol were added and the solution was placed at −80° C. for 20 min. The pellet was then centrifuged at 12,800 RPM for 10 min, decanted, washed with cold ethanol twice and dried.

To anneal the pieces, 18 μl of water were added to dissolve the pellet, the mixture heated in boiling water and cooled to room temperature slowly (∼10 min). At this point were added 3 μl of 10× KB-TS, 3 μl of 10 mM ATP and 3 μl of T4 DNA ligase (New England Biolabs; 40,000 units per ml). After 30 min at 14° C., the solution was dried and purified on a 10% denaturing polyacrylamide gel as described above for fragment 1. (Yield≃75 pmoles.)

c. Synthesis of DNA on a 2'-nitrobenzyluridine control pore glass support.

The 5'-dimethoxytrityl 2'-nitrobenzyluridine derivative of control pore glass (long chain alkylamino; Pierce Chemical Company) was prepared by Cruachem, Bend Oregon, according to Gough et al., *Tetrahedron Lett.* (1981) 22:4177. Oligonucleotide synthesis was carried out on an automatic synthesizer (Warner et al., *DNA* 3, in press).

The 2'-nitrobenzyl functionality was removed by U.V. irradiation as described by Ohtsuka et al., *Nucleic Acids Res.* (1974) 1:1351, except that a 2100 watt mercury bulb was employed. Five min irradiation in a pyrex cuvette was used for all samples (approximately 14.5 μmoles of 2'-nitrobenzyluridine).

A sequence corresponding to

5'TTCCATGGCTGCTAGGCTGTACTG-
CCAACTGGATCCTTCGCG-
GGACGTCCTTTGTTTACGrU 3'

(fragment 7) was produced in this manner and used for the coupling described below.

II. Attachment of DNA by the 3' end to solid supports.

a. Synthesis of thiosemicarbazido control pore glass (TSC-CPG).

Isothiocyanate control pore glass (Pierce Chemical) was modified with hydrazine to yield the thiosemicarbazido derivative as follows. 400 mg of isothiocyanate CPG was placed in a 50 ml round bottom flask. 25 ml of dimethylsulfoxide, 200 μl of distilled pyridine and 500 μl of a 0.6% hydrazine in dimethylsulfoxide solution were added (see, for example, J. Bauman et al., *J. of Histochem. and Cytochem.* (1981) 29:227). After 18 h with occasional mixing in the dark, the support was washed with 50 ml each of dimethylsulfoxide, pyridine, methanol and 2 L of 0.01M Tris, pH 7.5.

b. Attachment of fragment 7 to the solid support.

Approximately 2000 pmoles of fragment 7 was dried from water by evaporation. To this was added 100 μCi of γ$^{32}$P-ATP (New England Nuclear), 2 μl of 10× KB (0.5M Tris HCl pH 7.8, 100 mM MgCl2, 100 mM DDT), 1 μl (8U) T4 kinase (New England Nuclear). After 30' at 37° C., the solution was diluted to 1 ml with gel elution buffer and SEP-PAK de-salted as described above. Fragment 7 (20 μl, 982 pmoles) was treated with 20 μl of 1mM sodium periodate (Sigma) in 0.01M Tris-HCl, pH 8.0 for 1 h at 0° C. in the dark. To this was added 10 mg of TSC-CPG in 100 μl of 0.1M sodium acetate, pH 5.6 and the mixture allowed to set for 1 h at 0° C. in the dark, and then at 4° C. overnight.

In order to block the remaining thiosemicarbazido functionalities, periodate oxidized ATP was used. A 20 μl sample of 100 mM ATP was treated with 20 mg of sodium periodate in 100 μl of 0.01M Tris-HCl, pH 8.0. After 1 h in the dark, 45 μl of the solution was added to the 10 mg of fragment 7-TSC-CPG in 150 μl of 0.1M sodium acetate. After 6 h at 4° C., the support was washed extensively with 4× standard sodium citrate (SSC).

Based on the incorporated counts, 13% of fragment 7 (128 pmoles) were attached to the glass support.

III. Attachment of 5' ends of DNA to solid supports.

a. Preparation of bromoacetyl control pore glass (BA.0CPG).

Synthesis of O-bromoacetyl N-hydroxysuccinimide was carried out approximately as described by Cuatrecasas, *J. Biol. Chem.* (1974) 245:3059.

A mixture of 347 mg of bromoacetic acid and 345 mg of N-hydroxysuccinimide (Sigma) was made up in 20 ml of distilled dioxane. To this mixture was added 532 mg of dicyclohexylcarbodiimide. After 70 min of shaking at room temperature, the cloudy solution was filtered through glass-wool.

To 500 mg of long chain alkylamino control pore glass (Pierce Chemical; 0.1 meq/g) was added 100 ml of 0.10M sodium phosphate, pH 7.6. The slurry was placed on ice and the O-bromoacetyl N-hydroxysuccinimide solution was slowly added. After 30' with occasional stirring, the BA-CPG was washed with 5 L of 0.1M NaCl.

The number of equivalents of bromoacetate on the support was determined with a 5',5'-dithiobis(2- nitrobenzoic acid) acid (DTNB) test (Butterworth et al., *Arch. Biol. Biophysl.* (1967) 118:716). Stock solutions containing 200 mg of DTNB in 50 ml of water and 114 mg of 2-mercaptoethylamine in 100 ml of water were prepared. BA-CPG (10 mg) was racted with 10 μl of the 2-mercaptoethylamine solution plus 500 μl of 0.05M sodium phosphate at pH 8.0 for 10 min at room temperature. The solution was then tested with 100 μl of DTNB and the visible spectrum was recorded ($E = 1.36 \times 10^4$ mol$^{-1}$cm$^{-1}$ at pH 8). A control was run with 2-mercaptoethylamine without BA-CPG. From the amount of 2-mercaptoethylamine lost upon treatment with BA-CPG, it was determined that BA-CPG contained 10 mmoles bromoacetate per mg.

b. 5' attachment of DNA to BA-CPG.

To 10 μl (333 pmoles) of fragment 3 (see above) was added 10 μl of 3-$^{35}$S-ATP (adenosine 5'-0-(3-thiotriphosphate; 0.25 mCi; New England Nuclear)), 2–5 μl of 10× KB and 1 μl (8U) of T$_4$ polynucleotide kinase. After 30 min at 37° C., 1 μl of 50 mM 3-S-ATP (lithium salt; P.-L. Biochemicals) and 1 μl (8U) T$_4$ kinase were added. After an additional 30 min at 37° C., the fragment was gel isolated as described above (yield 266 pmoles). Samples were counted on a Beckman LS7000 liquid scintillation counter in Atomlite (New England Nuclear).

A 5 mg sample of BA-CPG was washed by centrifugation 3 times with water and 2 times with 0.10M sodium phosphate, pH 7.6. The 5'-thiophosphate fragment 2 was dissolved in 100 μl of the phosphate buffer and added to the washed BA-CPG. The slurry was mixed by rotation on a rotary evaporator for 2 h at room temperature. The solution was decanted and discarded. In order to block the remaining bromoacetate functionalities, the support was treated with 200 μl of 50 mM sodium phosphate, pH 8.0 and 50 μl of 2-mercaptoethanol for an additional 2 h. Subsequently the solution was decanted and the support was extensively washed with 4× SSC (yield ≈10 pmoles per mg of CPG).

Synthesis of Horseradish Peroxidase-DNA Conjugates.

a. Purification by Elutip.

Horseradish peroxidase (HRP) (2 mg; Type VI, Sigma; 10,000 U/38 mg) was dissolved in 0.5 ml of 0.1M sodium phosphate buffer, pH 7.5. O-bromoacetyl N-hydroxysuccinimide (15 μl) was added to the above solution and reaction allowed to proceed for 30 min at room temperature. The solution was passed over a PD-10 Sephadex G-25M column (Pharmacia) that had previously been equilibrated with 30 ml of 0.1M sodium phosphate, pH 7.5. The brown fraction (1–1.2 ml) was collected. Fragment 8 (5' to 3', GGTATTGTT-GAACAATGTTGTACTTCTATTTG) that had previously been 5'-thiophosphorylated with 3'-$^{35}$S-ATP as described above and dried (30 pmoles) was taken up in 50 μl of the phosphate buffer. To this thiophosphorylated fragment 8 solution was added the functionalized HRP and the mixture allowed to set for 30 min at room temperature. The mixture was passed over an Elutip-d (Schleicher and Schuell) column. The peroxidase-DNA conjugate is eluted in the void volume (26% of the counts were recovered). A control experiment conducted as described above but using 5'-$^{32}$P-phosphate labeled fragment 8 showed less than 0.5% of the counts were eluted under these conditions.

b. Separation by gel.

A peroxidase conjugate of fragment 9 (5' to 3', TTGAAGAACTACGGTTTGTTGTCTTGTTT-CAGAAAGGACTTGCACAAGACCCAAACC) was produced as above except that 360 pmoles of bromoacetyl horseradish peroxidase was combined with 156 pmoles of fragment 9 in 120 μl of 0.025M sodium phosphate pH 7.5. Instead of passing over an Elutip-d column, the mixture was evaporated to dryness, suspended in 1 82 l of 75% glycerol, 10 μl of H$_2$O and 1 μl of 1% bromophenol blue. This material was then run on a 10% native protein gel (Lindle, et al., *Methods in Enzymol.* (1983) 92:309). A control experiment with 5'-$^{32}$p-phosphate fragment 9 was also run. The enzyme-DNA conjugate was well resolved from the unconjugated peroxidase as a faster running $^{35}$S-labeled species. The gel was stained with 100ml of 10 mM Tris-HCl, pH 7.5, 50 mM NaCl, 60 μl of 30% H$_2$O$_2$ to which was added 60 mg of 4-chloro-1-naphthol dissolved in 20 ml of cold methanol. Since this stain is based on the horseradish peroxidase activity, it was possible to show that the peroxidase-DNA conjugate was itself active. No new active species was produced with the $^{32}$P-fragment 9 control.

c. Hybridization of DNA-peroxidase to complementary DNA.

5'-Thiophosphorylated fragment 11 (5' to 3', CCAA-GAGCTGGTCAAATCTTGAAGCAAACCTAC-GACAAGTTCGACACCAACATGAGATCTGAC-GACGCTTTG) was $^{32}$P-labeled as above. A 10% excess of fragment 12 (with reference to fragment 11) was added to the reaction mixture of 5'-thiophosphate fragment 11 plus bromoacetyl peroxidase. The solution was heated to 60° C. for 3 min and cooled to room temperature. A control was performed with fragment 12 plus bromoacetyl enzyme without 5'-thiophosphate fragment 11. A gel was run as before and the reaction mixture of fragment 11 plus bromoacetyl enzyme was run as a standard. The lane of fragment 12 plus enzyme and fragment 11 revealed a new slower running band (relative to the fragment 11-peroxidase conjugate) that contained $^{32}$P label. This band was also positive for peroxidase activity. No enzyme positive-$^{32}$P labeled band was found for the fragment 12-peroxidase control.

V. Assay.

The fragments in this assay represent a model system and comprise a portion of the Hepatitis B virus genome extending about 60 bases in the 5'- (fragment 3) and 3'-direction (fragment 2) from the BamHI site at base no. 1403 of HBV DNA. The analyte, fragment 4, is complementary to the 3' end of fragment 3 and the 5' end of fragment 2. The solid-supported fragment 3 was produced as described in Section IIIb. Fragment 2 was 5' labeled with γ-$^{32}$P-ATP according to the initial part of Section IIb (as applied to fragment 7).

a. Hybridization, Probe Capture.

Approximately 3 pmoles of a suspension of solid-supported fragment 3 (0.3 mg) and 5 pmoles of $^{32}$P-fragment 2 (in 10 μl H$_2$O) were used in each experiment. Appropriate quantities of reagents (see Table 1 below) were added to give a final volume of 50–100 μl, heated to 90° C. and cooled to room temperature over a 1 h period. After washing with 4×xSSC at room temperature, samples of the solid support were Chernenkov counted on a Beckman LS7000 liquid scintillation counter.

TABLE 1

| | pmole of Fragment 4, μl | μl of 20 × SCC | μl H₂O | CPM Bound |
|---|---|---|---|---|
| A | 0,0 | 8 | 20 | 31,260 |
| B | 1,10 | 8 | 10 | 132,293 |
| C | 0.5,5 | 8 | 15 | 113,039 | b. Restriction Cleavage Release.

Typically, the solid support after probe-capture as described above is washed with BamHI buffer (20 mM Tris-HCl, pH8.0, 7 mM MgCl₂, 100 mM NaCl, 2 mM 2-mercaptoethanol) twice and resuspended in 20 μl of the same buffer. To this 1 μl of BamHI (BRL; 5000 Units/715 μl) is added and mixed. After 30 min incubation at 37° C. the supernatant and one water wash are removed from the tube containing the settled solid support and counted. An additional 20 μl of buffer and 2 μl of enzyme are then added and left overnight at 37° C. The supernatant and one water wash are counted as before. Controls without enzyme are also run.

TABLE 2

| | Initial CPM on Support | CPM released after 30 min | CPM released after 18 h |
|---|---|---|---|
| Sample 1 w/enzyme | 69660 | 2064 | 10513 |
| Sample 1 w/o enzyme (control) | 67353 | 536 | 2524 |
| Sample 2 w/enzyme | 34982 | 1848 | 6336 |
| Sample 2 w/o enzyme (control) | 44113 | 504 | 2191 |

It is evident from the above results, that the subject method provides for a simple, rapid and accurate approach for detecting specific polynucleotide sequences from diverse sources. The method provides for high sensitivity and great flexibility in allowing for different types of labels which involve detectable signals which have been employed in immunoassays. Thus, the subject method can be readily adapted to use in conventional equipment for immunoassays which are capable of detecting radioactivity, light absorption in spectrophotometers and light emission in fluorometers or scintillation counters. The subject method is applicable to any DNA sequence and can use relatively small probes to reduce false positives and minimize undesirable heteroduplexing. By cleavage of the label from the support for measurements, background values can be greatly reduced, since the reading can occur away from the support. Also, there is a further redirection in background due to the necessity to cleave the label from the polynucleotide chain. The subject method can therefore provide for the accurate and economical determination of DNA sequences for diagnosing disease, monitoring hybrid DNA manipulations, determining genetic traits, and the like.

Although the foregoing invention has been described in some detail by way of illustration and example for purposes of clarity of understanding, it will be obvious that certain changes and modifications may be practiced within the scope of the appended claims.

What is claimed is:

1. A method for detecting the presence of an oligonucleotide sequence of interest in a nucleic acid analyte present in a nucleic acid sample, said method comprising:
combining under hybridizing conditions said nucleic acid sample with a polynucelotide reagent, wherein one of said sample or a component of said reagent is bound to a support and hybridization of said analyte and said polynucleotide reagent results in a label being bound to said support through a selectable cleavage site, wherein said selectable cleavage site is a restriction site resulting from the formation of a duplex at the oligonucleotide sequence of interest;
substantially freeing said support of label bound to said support other than through said selectable cleavage site;
cleaving said cleavage site with a restriction endonuclease which recognizes said site; and
detecting label free of said support.

2. A method according to claim 1, wherein said hybridization is effected through the binding of at least 4 complementary base pairs.

3. A method according to claim 1, wherein said polynucelotide reagent comprises a labeled polynucleotide bound to a support.

4. A method according to claim 1, wherein said polynucleotide reagent comprises a first polynucleotide bound to a support and a labeled second polynucleotide, wherein said first and second polynucleotides have oligonucleotide sequences complementary to sequences present in said analyte to form duplexes under said hybridizing conditions, at least one of said oligonucleotide sequence being a sequence of interest, wherein (1) either of said duplexes defines a restriction site, as said selectable cleavage site and said cleavage is with a restriction endonulease which recognizes said site, or (2) said label is linked to said polynucleotide through a selectable cleavage site and said cleavage is by cleaving said selectable cleavage site enzymatically or with light.

5. A method according to claim 1, wherein said nucleic acid sample is bound to said support and said polynucleotide reagent is labeled polynucleotide.

6. A method according to claim 1, wherein said label is a radionuclide.

7. A method according to claim 1, wherein said label is a fluorescer.

8. A method according to claim 1, wherein said label is an enzyme.

9. A method according to claim 1, wherein said label is an enzyme substrate or cofactor.

10. A method according to claim 1, wherein there is more than one label bound to said support through a plurality of selectable cleavage sites; and
a plurality of cleavage sites are cleaved.

11. A method according to claim 1, wherein said hybridization is effected through the binding of at least 12 complementary base pairs.

12. A method for detecting the presence of an oligonucleotide sequence of interest in a nucleic acid analyte present in a nucleic acid sample, said method comprising:
combining under hybridizing conditions in an aqueous medium, said nucleic acid sample with a polynucleotide reagent, where one of said sample or a component of said reagent is bound to a support and hybridization of said analyte and said polynucleotide reagent results in a label being bound to said support through a selectable cleavage site, wherein said selectable cleavage site is a restriction site resulting from the formation of a duplex at the oligonucleotide sequence of interest;

separating said support having bound polynucleotide reagent and nucleic acid analyte from said aqueous medium;

washing said support with a medium of different hybridizing stringency from said aqueous medium to remove label bound to said support other than through said selectable cleavage site;

cleaving said cleavage site with a restriction endonuclease which recognizes said site; and detecting label free of said support.

13. A method according to claim 11, wherein said polynucleotide reagent comprises a labelled polynucleotide bound to a support.

14. A method according to claim 11, wherein said polynucleotide reagent comprises a first polynucleotide bound to a support and a labeled second polynucleotide, wherein said first and second polynucleotides have oligonucleotide sequences complementary to sequences present in said analyte to form duplexes, at least one of said oligonucleotide sequences being a sequence of interest, wherein (1) either of said duplexes defines a restriction site as said selectable cleavage site and said cleavage is with a restriction endonuclease which recognizes said site, or (2) said label is linked to said polynucleotide through a selectable cleavage site.

15. A method according to claim 14, wherein said nucleic acid sample is bound to said support and said polynucleotide reagent is labeled polynucleotide.

16. A method according to claim 12, wherein said hybridization is effected through the binding of at least 4 complementary base pairs.

17. A method according to claim 12, wherein said hybridization is effected through the binding of at least 12 complementary base pairs.

18. A reagent for detecting the presence of an oligonucleotide sequence of interest in a nucleic acid analyte present in a nucleic acid sample, comprising a polynucleotide sequence bound proximal to one end to a support and proximal to the opposite end to a label capable of providing, directly or indirectly, a detectable signal, said polynucleotide sequence having a sequence which when duplexed with said sequence of interest defines a selectable cleavage site cleavable by a restriction endonuclease which recognizes said site.

19. A reagent composition for detecting the presence of an oligonucleotide sequence of interest in a nucleic acid analyte present in a nucleic acid sample, comprising a first polynucleotide having a first oligonucleotide sequence complementary to a first portion of said sequence of interest; and a labeled second polynucleotide, wherein said label provides, directly or indirectly a detectable signal, said second labeled polynucleotide having a second oligonucleotide sequence complementary to a second portion of said sequence of interest, said first and second portions comprising the entirety of said sequence of interest, wherein a continuous duplex may be formed, under hybridizing conditions, between said first oligonucleotide sequence and said first portion of said sequence of interest and between said second oligonucleotide sequence and said second portion of said sequence of interest, said continuous duplex containing a selectable cleavage site cleavage by a restriction endonuclease which recognizes said site.

20. A deoxyribonucleotide reagent comprising a deoxyribonucleotide sequence of at least four bases joined to a glass particle support through the reaction product of a semicarbazide and the dialdehyde reaction product of a ribonuceleotide and an oxidant, wherein said at least four bases are selected so as to form a duplex with a sequence of interest under hybridizing conditions, the duplex so formed containing a selectable cleavage site cleavable with a restriction endonuclease which recognizes said site.

21. A deoxyribonucleotide reagent comprising a deoxyribonucleotide sequence of at least four bases joined to a glass support through a phosphothiacetamide link, said link formed by reaction between a bromoacetamide substitutent on said glass support and a 5'-thophosphate moiety on said deoxyribonucleotide reagent, wherein said at least four bases are selected so as to form a duplex with a sequence of interest under hybridizing conditions, the duplex so formed containing a selectable cleavage site cleavable with a restriction endonuclease which recognizes said site.

22. The reagent composition of claim 21, wherein said duplex is formed from at least 12 complementary base pairs.

23. A reagent composition for detecting the presence of an oligonucleotide sequence of interest in a nucleic acid analyte present in a nucleic acid sample, comprising a first component which is a polynucleotide bound to a support and a second component which is a labeled second polynucleotide, wherein said label provides, directly or indirectly, a detectable signal, wherein said first and said second polynucleotides have oligonucleotide sequences complementary to sequences present in said analyte which form duplexes with said analyte under hybridizing conditions, at least one of said oligonucleotide sequences being complementary to a sequence of interest, wherein one of said duplexes defines a selectable cleavage site cleavable by a restriction endonuclease which recognizes said site.

24. The reagent composition of claim 23, wherein said duplexes are formed from at least 4 complementary base pairs.

25. The reagent composition of claim 23, wherein said duplexes are formed from at least 12 complementary base pairs.

* * * * *

UNITED STATES PATENT AND TRADEMARK OFFICE
CERTIFICATE OF CORRECTION

PATENT NO. : 4,775,619
DATED : October 4, 1988
INVENTOR(S) : Mickey S. Urdea It is certified that error appears in the above-identified patent and that said Letters Patent is hereby corrected as shown below:

In column 18, line 38, (claim 4) delete "or with light".

Signed and Sealed this

Sixth Day of July, 1993

Attest:

MICHAEL K. KIRK

*Attesting Officer*     Acting Commissioner of Patents and Trademarks

UNITED STATES PATENT AND TRADEMARK OFFICE
CERTIFICATE OF CORRECTION

PATENT NO.   : 4,775,619
DATED        : October 4, 1988
INVENTOR(S)  : Mickey S. Urdea It is certified that error appears in the above-identified patent and that said Letters Patent is hereby corrected as shown below:

Column 19:
    In Claim 13, line 1, please delete "11" and insert therefor --12--.

In Claim 14, line 1, please delete "11" and insert therefor --12--.

Column 20:
    In Claim 21, line 3, after "glass" please insert --particle--.

In Claim 21, line 3, please delete "phosphothiacetamide" and insert therefor --phosphothiocetamide--.

In Claim 21, line 5, after "glass" please insert --particle--.

In Claim 21, line 5, please delete "thophosphate" and insert therefor --thiophosphate--.

In Claim 23, line 4, after "ing" please insert --: --.

UNITED STATES PATENT AND TRADEMARK OFFICE
CERTIFICATE OF CORRECTION

PATENT NO. : 4,775,619
DATED : October 4, 1988
INVENTOR(S) : Mickey S. Ureda

It is certified that error appears in the above-indentified patent and that said Letters Patent is hereby corrected as shown below:

Column 20, claim 23, line 5, after "support" please insert --;--.

Signed and Sealed this

Ninth Day of November, 1993

Attest:

BRUCE LEHMAN

*Attesting Officer*  *Commissioner of Patents and Trademarks*

UNITED STATES PATENT AND TRADEMARK OFFICE
CERTIFICATE OF CORRECTION

PATENT NO. : 4,775,619

DATED : 4 October 1988

INVENTOR(S) : MICKEY S. URDEA

It is certified that error appears in the above-identified patent and that said Letters Patent is hereby corrected as shown below:

Column 19:
    In claims 13 and 14, line 1 of each claim, replace "11" with --12--.

Signed and Sealed this

Twenty-first Day of December, 1993

Attest:

BRUCE LEHMAN

Attesting Officer     Commissioner of Patents and Trademarks